(12) United States Patent
Mendelovici et al.

(10) Patent No.: US 9,752,975 B2
(45) Date of Patent: *Sep. 5, 2017

(54) METHOD AND APPARATUS FOR DETERMINING CLEANLINESS OF A SAMPLE

(71) Applicant: PERSYS TECHNOLOGY LTD., Kiryat Gat (IL)

(72) Inventors: Leo Mendelovici, Mavaseret Ziyon (IL); Gideon Drimer, Herzeliya (IL); Yitzhak Vanek, Los Gatos, CA (US)

(73) Assignee: PERSYS TECHNOLOGY LTD., Kiryat Gat (IL)

( * ) Notice: Subject to any disclaimer, the term of this patent is extended or adjusted under 35 U.S.C. 154(b) by 77 days.

This patent is subject to a terminal disclaimer.

(21) Appl. No.: 14/991,955

(22) Filed: Jan. 10, 2016

(65) Prior Publication Data
US 2016/0195467 A1 Jul. 7, 2016

Related U.S. Application Data

(63) Continuation-in-part of application No. PCT/US2013/050148, filed on Jul. 11, 2013.

(51) Int. Cl.
| | |
|---|---|
| *G01N 21/00* | (2006.01) |
| *G01N 15/14* | (2006.01) |
| *G01N 15/06* | (2006.01) |
| *G01N 15/02* | (2006.01) |
| *G01N 15/00* | (2006.01) |

(52) U.S. Cl.
CPC ..... *G01N 15/1429* (2013.01); *G01N 15/0205* (2013.01); *G01N 15/0612* (2013.01); *G01N 2015/0046* (2013.01); *G01N 2015/1486* (2013.01)

(58) Field of Classification Search
CPC ...... G01B 9/02; G01B 11/002; G01B 11/026; G01D 5/266; G01D 5/38
USPC .......................................................... 356/338
See application file for complete search history.

(56) References Cited

U.S. PATENT DOCUMENTS

| | | | | |
|---|---|---|---|---|
| 5,895,869 | A * | 4/1999 | Von Behrens ..... | G01N 15/1404 73/865.5 |
| 5,914,454 | A * | 6/1999 | Imbaro .............. | B01D 53/1418 261/79.2 |
| 6,327,021 | B1 | 12/2001 | Higashiguchi | |
| 6,474,355 | B1 | 11/2002 | Jirawat et al. | |
| 7,181,952 | B2 * | 2/2007 | Ditch .................... | G01F 1/68 73/29.01 |
| 7,437,908 | B2 | 10/2008 | Bae et al. | |

(Continued)

FOREIGN PATENT DOCUMENTS

| | | |
|---|---|---|
| JP | 2006153709 | 6/2006 |
| KR | 100614101 | 8/2006 |

*Primary Examiner* — Tarifur Chowdhury
*Assistant Examiner* — Md M Rahman
(74) *Attorney, Agent, or Firm* — Daniel J. Swirsky; AlphaPatent Associates Ltd.

(57) ABSTRACT

Determining cleanliness of a sample by providing a continuous flow of clean air into a chamber through a HEPA filter, taking a reference reading of particle counts while the chamber is empty, introducing the sample into the chamber and taking a first reading of a particle count received from all sides of the sample in the chamber to determine loose particles in a particle size range of 0.1 microns up to 5 microns associated with the sample.

23 Claims, 12 Drawing Sheets

(56) References Cited

U.S. PATENT DOCUMENTS

2007/0023694 A1 2/2007 Kim et al.
2011/0068263 A1* 3/2011 Wouters .............. H01J 49/0445
　　　　　　　　　　　　　　　　　　　　　　　250/282

* cited by examiner

METHOD AND APPARATUS FOR DETERMINING CLEANLINESS OF A SAMPLE

CROSS-REFERENCE TO RELATED APPLICATIONS

This application is a continuation-in-part of International Application No. PCT/US2013/050148, which has an international filing date of Jul. 11, 2013.

FIELD

Embodiments of the invention provide a method and apparatus for particle detection. More particularly, embodiments of the invention provide a method and apparatus for determining cleanliness of a sample.

BACKGROUND

Contamination detection has become increasingly significant, particularly with rapid evolution of high-tech industries. For example, semiconductor industry has developed technology for precisely producing microelectronic devices and integrated circuits. In order to reliably produce such products, highly stringent contamination standards must be maintained in production facilities of such products.

In an effort to control contamination during a production process, clean rooms are frequently used. A clean room is a room in which air filtration, air distribution, utilities, materials of construction, equipment, and other operating procedures are specified and regulated to control airborne particle concentrations to meet appropriate airborne particulate cleanliness classifications. Clean rooms are used extensively in semiconductor manufacturing, biotechnology, pharmaceutical, disk drive, aerospace and other fields that are very sensitive to environmental contamination.

It is important to monitor and maintain the cleanliness/contamination levels in the clean rooms. Further, for maintaining the cleanliness/contamination levels in the clean room, it is important to test/inspect a sample for cleanliness standard, before sending the sample to the clean room. Hence, cleanliness of a new sample coming to the clean room environment is very important.

In addition, in the mentioned industries it is customary to carry out preventive maintenance of manufacturing tools such as sputtering, CVD, etch, and other tools. As part of this procedure some of the parts require renovation and cleaning. Therefore, it is of high importance to be able to test cleanliness of the part before reinstalling it to a machine.

Conventionally, visual inspection techniques have been used with ultraviolet or oblique white light. Ultraviolet light is employed to take advantage of the fact that certain organic particles fluoresce. Alternatively, white light is shined towards a test surface at an angle so as to produce reflections that can be visualized. While the white light technique is slightly more sensitive than the ultraviolet technique, they both suffer from a common limitation. These visual inspection techniques only allow a cursory inspection of the sample or surface conditions. Further, the visual inspection techniques, at best, only detect particles that are larger than twenty microns. If, it is desirable or requirement to detect particles that are less than one micron, conventional techniques fails to achieve the goal. Furthermore, these conventional techniques are very tedious and time consuming.

Other conventional techniques include particle counters, which are intended for measuring particles on the surface. However, one of the main disadvantages of this technique is that it is localized and does not account for the complete sample.

Yet another conventional technique include Liquid Particle Counters, which are intended for measuring particles removed from a sample after flowing clean water through the sample. However in this case the sample cannot be further used and needs to be either dissected or processed (cleaned) again.

Hence, there is a need for apparatus and method that can determine cleanliness of a sample, before shipping or taking the sample to clean room environment. Further, there is a need for a method and apparatus that can determine the cleanliness of the sample in a convenient and effective manner.

SUMMARY

Embodiments in accordance with the invention provide a method for determining cleanliness of a sample. The method includes taking a reference reading of the empty chamber so a background or blank value is determined before introducing the sample into the chamber and while a constant flow of clean air, such as clean dry air (CDA) from the HEPA filter-unit flows through the chamber constantly. The method further includes taking a first reading of particles count of a sample placed into a chamber. The next step includes directing a stream of air over the sample, and taking a second reading of particles count of the sample. The method further includes calculating a difference between the first reading and the second reading, and determining a cleanliness of the sample based upon the difference of the readings, taking into account the blank reading.

There is thus provided according to an embodiment of the invention, a non-destructive method for determining cleanliness of a sample, the method including;

a) providing a continuous flow of clean air into a chamber; through the HEPA filter b) taking a reference reading of particle counts while the chamber is empty;

c) introducing the sample into the chamber;

d) taking a first reading of a particle count received from all sides of the sample in the chamber to determine loose particles in a particle size range of 0.1 microns up to 5 microns associated with the sample.

Additionally, according to an embodiment of the invention, the sample is a generally three-dimensional sample.

Furthermore, according to an embodiment of the invention, the method further includes;

e) directing a stream of ionized air over the sample;

f) taking a second reading of particles count of the sample; and g) calculating a difference between the first reading and the second reading thereby determining the cleanliness of the sample based upon the difference.

Moreover, according to an embodiment of the invention, a third reading is taken during the directing step and wherein the cleanliness of the sample is calculated based upon difference between the third reading and the second reading, or between the three readings, while taking into account the reference reading.

Further, according to an embodiment of the invention, the determining cleanliness method includes comparing a difference with a predetermined threshold.

Additionally, according to an embodiment of the invention, the difference represents an impurities particles count.

Importantly, according to an embodiment of the invention, the method further includes trapping the impurities particles released from the sample due to the stream of ionized air.

Furthermore, according to an embodiment of the invention, the method further includes analyzing the trapped particles to determine nature and chemical composition of the impurities particles.

Additionally, according to an embodiment of the invention, the sample is selected from at least one of a metal part, quartz part, ceramic part, and plastic part.

Further additionally, according to an embodiment of the invention, the sample is selected from at least one of a machine part, a tool, a clean room gown, a clean room glove a clean room towel, a silicon wafer, and a magnetic disk.

Furthermore, according to an embodiment of the invention, wherein the sample, once tested, is ready for use in a clean room following the method.

There is thus provided according to another embodiment of the invention, an apparatus for determining cleanliness of a sample, the apparatus including:

a chamber having a door and a sample holder or an integrated sample jig for holding both a sample in the chamber and providing a high velocity air stream, (100-300 m/s) over the sample; in the chamber;

a HEPA filter unit with a blower or a dome to provide CDA disposed above the chamber and in fluid connection with the chamber; the blower adapted to provide a constant flow to the chamber; and a set of nozzles activated by a set of valves to provide a stream of high velocity clean air or short pulses of high velocity clean air over the sample. The air to the nozzles is provided through in-line HEPA filter units a valve coupled to an electrostatic discharge device (ESD) for generating ionized air, in fluid connection with a nozzle set, located in the chamber, the nozzle set configured to direct a stream of air via the HEPA filter unit onto the sample;

a particle counter, coupled with the chamber, configured to count particles passed in a stream of air from the sample to the particle counter; and a programmable controller for operating the apparatus Additionally, according to an embodiment of the invention, the nozzle set includes a nozzle connected to an in-line HEPA filter unit.

Furthermore, according to an embodiment of the invention, the nozzle set includes a shower head connected to an in-line HEPA filter unit.

Moreover, according to an embodiment of the invention, the nozzle set includes a nozzle and a shower head connected to an in-line HEPA filter unit.

Additionally, according to an embodiment of the invention, the chamber further includes a filter detachably located in a filter holder for trapping particles released from the sample due to the stream of air by applying a vacuum through the filter.

Importantly, according to an embodiment of the invention, the filter is removable for analyzing the chemical composition of trapped particles.

Further, according to an embodiment of the invention, the valve is a Venturi valve for supplying a stream of clean air or ionized air.

Additionally, according to an embodiment of the invention, the particle counter is a laser type particle counter.

Moreover, according to an embodiment of the invention, the ESD device is adapted for activation by supplying a voltage thereto to provide a constant flow of ionized air to the chamber.

Additionally, according to an embodiment of the invention, the chamber and the particle counter are connected via a counter isokinetic probe.

Furthermore, according to an embodiment of the invention, the ESD device is located inside the chamber and adapted for activation by supplying a voltage thereto to provide a constant flow of ionized air to the chamber.

Yet further, according to an embodiment of the invention, the chamber further includes an electrostatic precipitator device (ESP) with a removable electron microscope holder coated with a detachable carbon sticker to which high voltage (5 KV) is applied in order to catch particles released from the sample for analyzing the chemical composition of trapped particles.

Embodiments in accordance with the invention further provide an apparatus for determining cleanliness of a sample. The apparatus includes a HEPA filter unit with a blower, a chamber, a nozzle set, and a particle counter. The chamber includes a sample holder for holding a sample. The nozzle set is located in the chamber, and is configured to direct a stream of clean air into the sample. The stream of clean air is operated through a frictionless device such as a Venturi valve to avoid generation of particles. The particle counter is coupled with the chamber, and configured to count particles released from the sample.

Embodiments in accordance with the invention further provide a method for determining cleanliness of a sample. The method includes taking a reference reading of the empty chamber as above, placing a sample into a chamber, and taking a first reading of particles count released from the sample. The method further includes directing a stream of ionized air over the sample, and taking a second reading of particles count released from the sample. The method further includes taking an additional reading while an electrostatic discharge device (ESD) is activated and calculating a difference between the readings to determine impurities particles count. The method further includes comparing the impurities particles count with a pre-determined threshold value, and determining a cleanliness of the sample based upon the comparison.

Further, the invention can provide a number of advantages depending on its particular configuration. First, embodiments of the invention provide a system and a method for testing cleanliness of equipment parts and other samples, which can work in a clean room environment only after a cleanliness testing procedure has been carried out. Further, the invention facilitates directly packing and shipping the samples, if they meet the cleanliness criteria. Hence, they may not require additional cleaning or drying procedures such as used in liquid particle counters (LPC), surface particle counters, or similar equipment.

Furthermore, the invention utilizes a conventional particle counter for determining cleanliness of a sample. Hence, the invention provides a convenient, simple, and effective method to determine cleanliness of the sample.

These and other advantages will be apparent from the disclosure of the invention contained herein.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible, utilizing alone or in combination, one or more of the features set forth above or described in detail below.

BRIEF DESCRIPTION OF THE DRAWINGS

The above and still further features and advantages of the invention will become apparent upon consideration of the following detailed description of embodiments thereof, especially when taken in conjunction with the accompanying drawings, and wherein.

Figure 1:
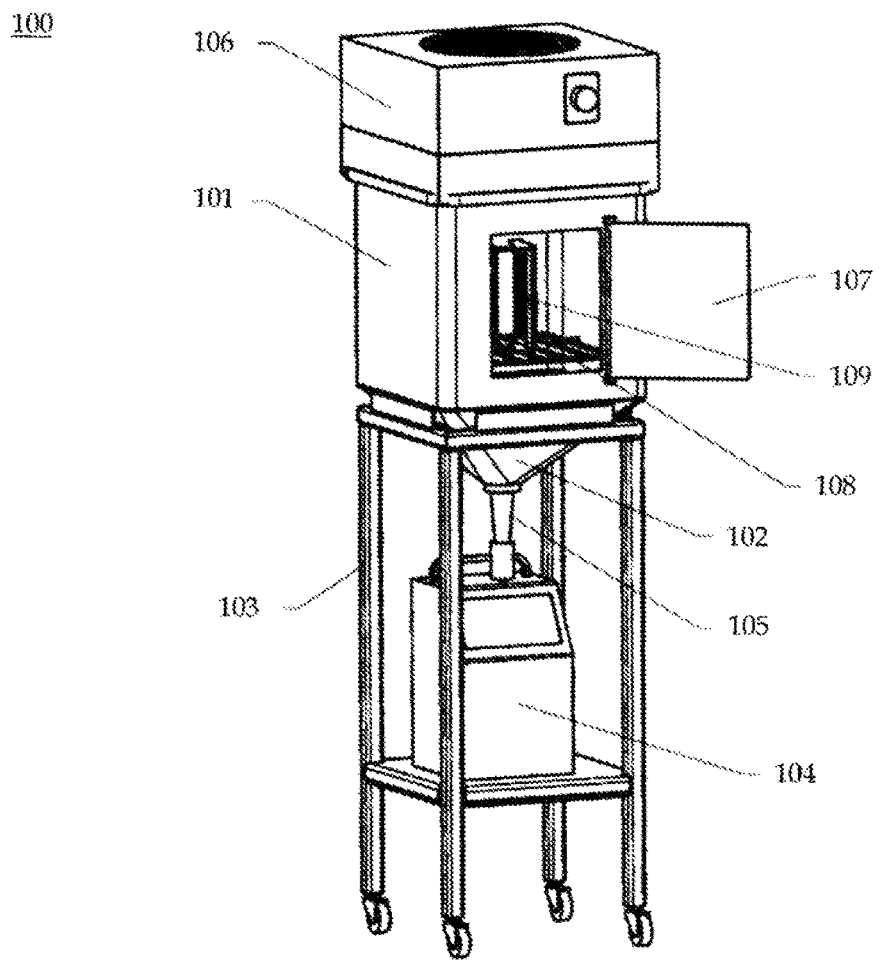
FIG. 1 shows a schematic diagram of front view of an apparatus, in accordance with an embodiment of the invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the drawing figures.

DETAILED DESCRIPTION

The invention will be illustrated below in conjunction with an exemplary method and apparatus for determining cleanliness of a sample. The invention is not limited to any particular type of method and apparatus or configuration of system elements. Those skilled in the art will recognize the disclosed techniques may be used in any method or system in which it is desirable to determine cleanliness of a sample.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine", "calculate" and "compute," and variations thereof, as used herein, are used interchangeably and include any type of methodology, process, mathematical operation or technique.

Figure 2:
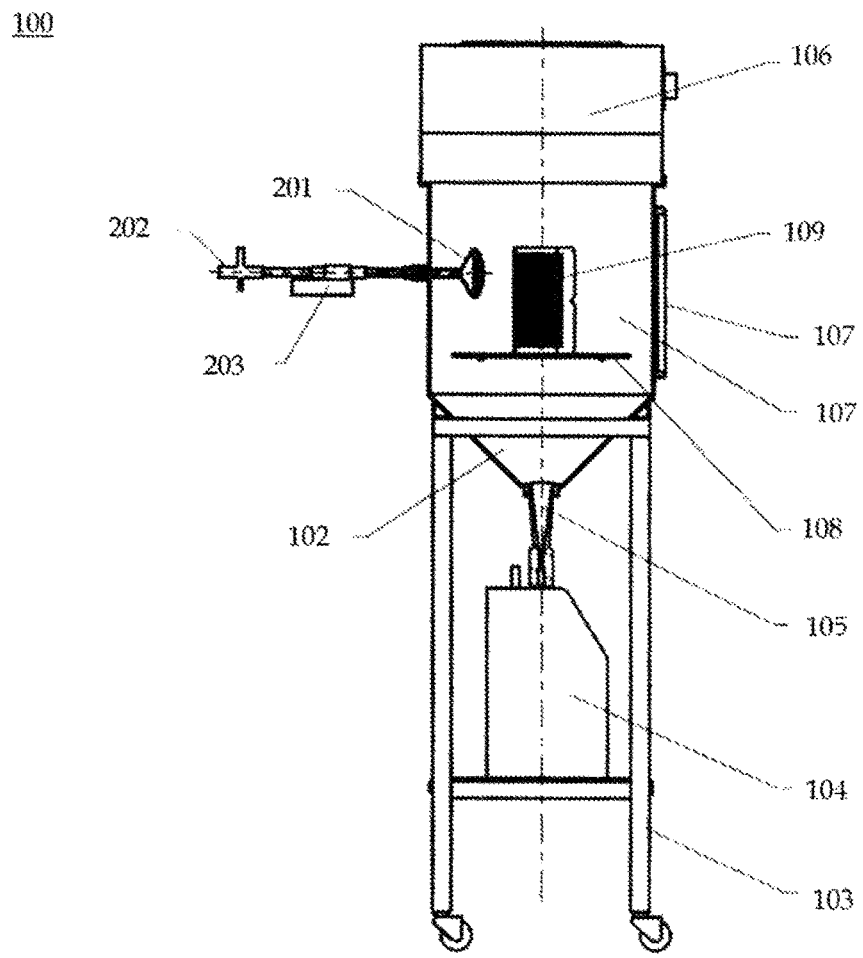
FIG. 2 shows a schematic diagram of side view of the apparatus according to an embodiment of the invention.
Figure 3:
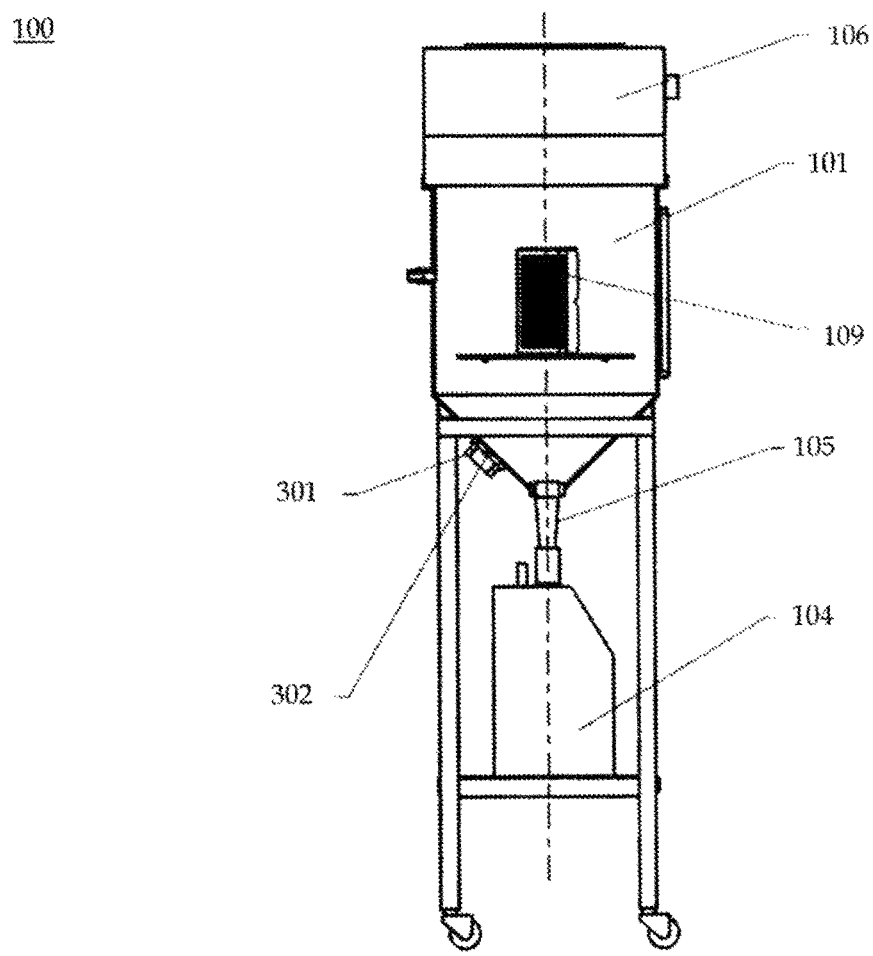
FIG. 3 shows another schematic diagram of side view of the apparatus according to an embodiment of the invention.

FIGS. 1, 2, and 3 show schematic diagrams of front view and side view of an apparatus 100 respectively, in accordance with an embodiment of the invention. The apparatus 100 includes a chamber 101 having a funnel shaped bottom section 102 supported by a stand 103. The chamber 101 is further coupled with a particle counter 104. In an embodiment of the invention, the chamber 101 and the particle counter 104 may be connected through a counter isokinetic probe 105. In another embodiment, the chamber 101 and the particle counter 104 may be connected through any other suitable means.

Further, the apparatus 100 includes a HEPA filter 106 mounted with a blower. In an embodiment, the HEPA filter 106 may be a high efficiency (HEPA) filter 106. The HEPA filter 106 may be used for supplying a constant flow of clean air into the chamber 101 with the help of the blower. Furthermore, the apparatus 100 includes a door 107 that may be kept in an open position to access a sample holder 108 present within the apparatus. The sample holder 108 may be used to hold a sample 109 in position within the apparatus. In an embodiment, the sample holder 108 is designed to properly hold various types of samples. It should be understood that the sample holder is adapted to hold samples which are generally two-dimensional or three-dimensional.

In the invention, the term "sample" relates to any machine part, tool, parts holders, wafers, disks, garments wipes, gloves etc that is used in a clean room environment.

In an embodiment, the particle counter 104 is configured to detect and count particles on all sides of the sample 109. The apparatus of the invention enables counting particles, which are released from surfaces of a generally two-dimensional sample into an air stream and passed into a particle counter. The apparatus of the invention enables counting particles, which are released from surfaces of a three-dimensional sample into an air stream and passed into a particle counter. Further, the particle counter 104 may be a single channel particle counter, and may detect and count particles of one particular size at a time.

The particle sizes detected by the methods and apparatus of the invention are in the range of 1 nm to 1000 micron, 10 nm to 100 micron, 100 nm to 20 micron or less than one micron. According to additional embodiments of the invention, the particle size range of particles detected by the methods and apparatus of the invention is 0.1 to 0.5 microns. According to additional embodiments of the invention, the particle size range of particles detected by the methods and apparatus of the invention is 1 to 5 microns.

In another embodiment, the particle counter 104 may be able to count multiple particle sizes. Further, in an embodiment, the particle counter 104 may be a typical laser type particle counter or may operate based upon light scattering, light obscuration, or direct imaging.

Further, the sample 109 may include a metal part, quartz part, ceramic part, and plastic part, which may be used in a clean room environment for various applications, for example, machine parts, tools, gowns, gloves, clean room towels, etc. In an embodiment, the chamber 101 may be manufactured from various materials including metals, such as aluminum, stainless steel, glass (e.g., quartz, borosilicate glass, etc.), plastics etc. In another embodiment, the chamber 101 may be manufactured from any other convenient fabrication material or a combination of these materials.

The chamber 101 of the apparatus further includes a nozzle 201 (as shown in FIG. 2) for directing a stream of air into the sample. The stream of air may further include a frictionless device such as a pinch valve or a Venturi valve 202. The pinch valve or the Venturi valve 202 may be used for supplying a stream of clean air or ionized air. The apparatus 100 further includes an electrostatic discharge device (ESD) 203 (as shown in FIG. 2) for generating ionized air. The ESD device 203 is coupled with the nozzle 201. The apparatus 100 may further include a frictionless device (e.g., Venturi valve 202) for supplying stream of clean air or a stream of ionized clean air. The ESD device 203 is further needed to be activated in order to generate ionized air. In an embodiment of the invention, air may constantly flow through the ESD device 203, and the ESD device 203 may be activated by supplying voltage.

In another embodiment of the invention, voltage may be constantly applied on the ESD device 203 and the ionized air flow out of the clean chamber, through the Venturi valve 202 (as described above) in to the chamber 101 and over the sample 109. Once activated, the ESD device 203 may direct the ionized air over the sample. In an embodiment of the invention, clean/ionized air constantly and continuously flows through the HEPA filter unit 106 into the chamber 101.

Further, in an embodiment of the invention, the apparatus 100 may include a filter holder 301 holding a filter 302 (as shown in FIG. 3). The filter 302 is detachably located in the filter holder 301 and can be used for trapping particles released from the sample 109 upon applying a vacuum through the filter 302. The filter 302 can be further removed from the filter holder 301 and the nature and chemical composition of the particles can be further determined by conventional analytical methods.

Figure 4A:
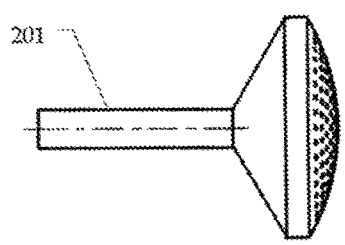
FIGS. 4A and 4B shows a typical set of nozzles for air injection.
Figure 4B:
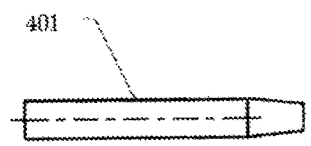

In an embodiment of the invention, as shown in the FIGS. 4A and 4B of the invention, the nozzle 201 may be in a shape of a shower head (as shown in FIG. 4A) or may be in a shape of a conventional nozzle (as shown in FIG. 4B). In another embodiment, the apparatus 100 may use a nozzle set having both the conventional nozzle and the shower head. In yet another embodiment, the nozzle 201 may be a nozzle set comprising a nozzle and/or a shower head. The nozzle set illustrated in FIGS. 4A and 4B are typically used for air injection.

Further, in an embodiment of the invention, the apparatus 100 may further include an electronic control system (now shown in Figure) that may be used by an operator to operate the apparatus. In another embodiment, a programmable controller (not shown in Figure) may be used to operate the apparatus or system.

Furthermore, in an embodiment of the invention, a personal computer (now shown in Figure) may be connected with the apparatus to control the operation of the system and acquire the readings of the particle counter 104, and further processing the readings to determine cleanliness of the sample 109 with appropriate software to control the system and acquire and process the readings.

Figure 5A:
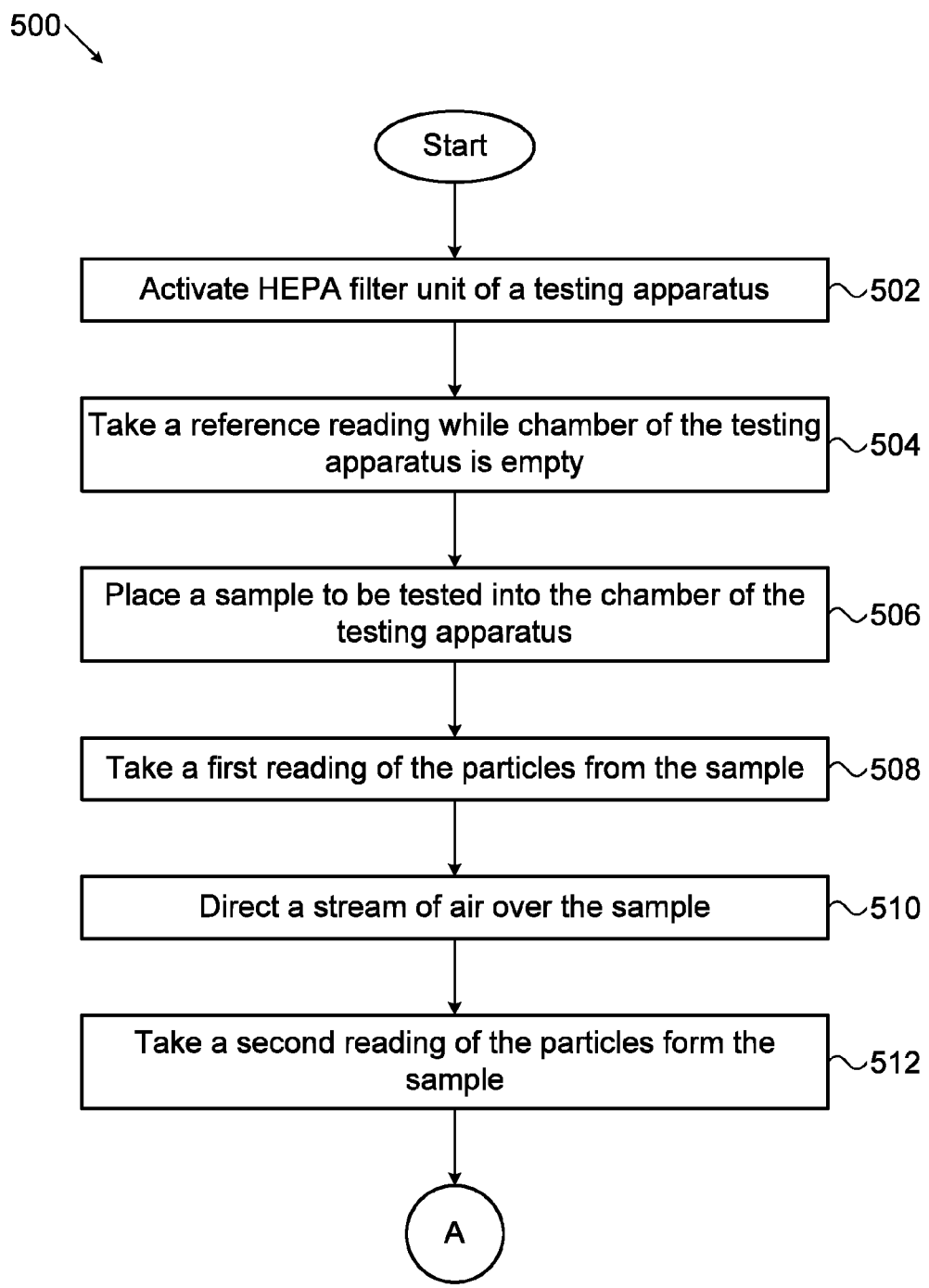
FIGS. 5A and 5B are a flowchart of a method for determining cleanliness of a sample, in accordance with an embodiment of the invention.
Figure 5B:
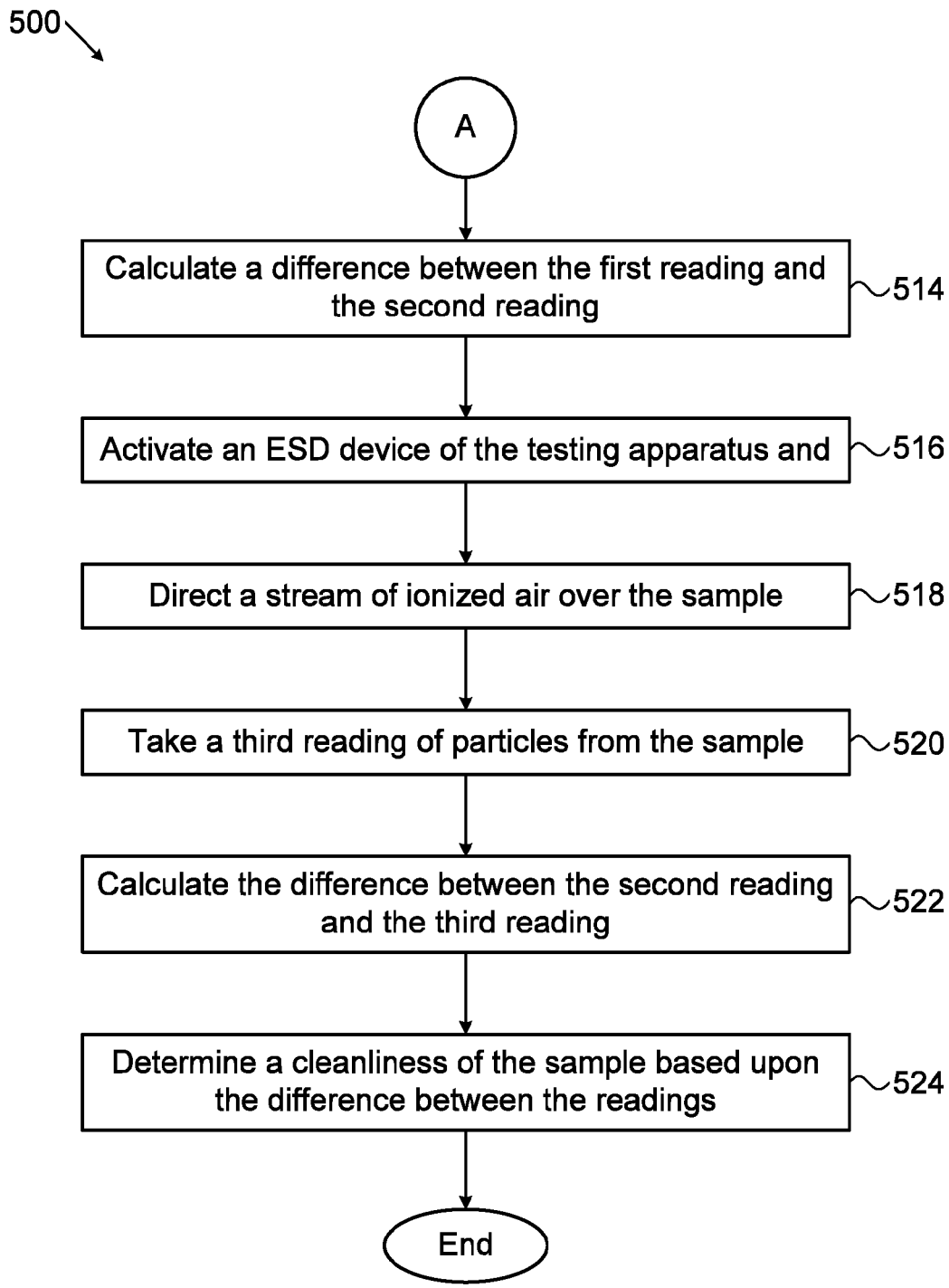

FIGS. 5A and 5B are a flowchart of a method 500 for determining cleanliness of a sample, in accordance with an embodiment of the invention. A sample (such as, sample 109) is placed into a chamber (such as, chamber 101) of a testing apparatus (such as, testing apparatus 100, as shown in FIGS. 1, 2, and 3) that is designed to test cleanliness of various samples. In an embodiment of the invention, the chamber 101 of the testing apparatus 100 may be manufactured from various materials including metals, such as aluminum, stainless steel, glass (e.g., quartz, borosilicate glass, etc.), plastics etc. In another embodiment, the chamber 101 may be manufactured from any other convenient fabrication material or a combination of these materials.

At step 502, HEPA filter unit 106 and a blower of the testing apparatus is activated. In an embodiment, the blower must be configured to blow a constant and continuous stream of clean air flow through the HEPA filter unit 106. Thereafter, at step 504, a reference reading is taken considering that the chamber 101 of the testing apparatus is empty. This reading may help in determining particles count within the apparatus before putting in a sample. In an embodiment, the reading may be taken by a particle counter (such as particle counter 104) of the testing apparatus. At step 506, a sample to be tested for cleanliness (such as the sample 109) is placed into the chamber 101 of the testing apparatus 100. Specifically, the sample 109 may be placed into a sample holder (such as the sample holder 108), which is present inside the chamber 101 of the testing apparatus. The sample 109 may include a metal part, quartz part, ceramic part, and plastic part, which may be used in a clean room environment for various applications, for example, silicon wafers, magnetic disks, machine parts, gowns, gloves, clean room towels, etc. In an embodiment, the sample holder 108 is designed to properly hold various types of samples.

At step 508, a first reading of particles count of the sample 109 (present inside the apparatus) is taken with the particle counter 104. The first reading of particles count of the sample 109 may represent the fraction of loose particles present in the sample. Thereafter, at step 510, a stream of clean air is directed over the sample 109. In an embodiment, a stream of ionized air may also be directed over the sample 109. An ESD device (such as ESD device 203) may be used to generate the ionized air. Further, the stream of air directed over the sample may release some additional contamination or impurities particles present (if present) on the sample 109.

At step 512, a second reading (after directing stream of air over the sample) of particles count released from the sample 109 is taken with the particle counter 104. The particles count noticed from the second reading may represent particles remaining in the sample 109 after release of some contamination/particles by directing a stream of clean air over the sample 109. In an embodiment, the readings of the particle count are taken as a function of time or after pre-determined time interval. Further, at step 514 (as shown in FIG. 5B), a difference between the first reading and the second reading is calculated. In an embodiment, the difference may determine contamination/impurities particles count released from the sample due to strike by the stream of air.

At step 516, the ESD device 203 is activated and at step 518 a stream of clean ionized air is directed over the sample. Thereafter, at step 520 an additional reading (third reading) of the particle count from the sample 109 is taken with the particle counter 104 (while the ESD device 203 is active). Then, at step 522, a difference between the second reading and the third reading is calculated. In an embodiment, the difference may determine contamination/impurities particles count released from the sample due to strike by the stream of clean ionized air.

At step 524, cleanliness of the sample 109 is determined based upon the difference between the measured readings. In an embodiment, the difference (i.e., contamination/impurities particle count) may be compared with a predetermined threshold value, and the cleanliness of the sample 109 may be determined based upon the comparison. For example, if the difference is less than the predetermined threshold value, the sample may be determined to be in a clean state. Otherwise, the sample may be determined to be in an unclean state. The predetermined threshold value may be set based upon cleanliness standard required in production facility or clean room. In an embodiment, the reference reading taken in the step 504 may be considered to determine a threshold value.

Furthermore, the description above is meant for illustration purposes only and different methodology can be used to determine the cleanliness of a sample. For example continuous readings of the particle counter can be recorded after placing the sample into the chamber, directing a stream of air over the sample, directing a stream of ionized air over the sample, etc. For the values recorded, a graph or table can be generated and the influence of each step can be determined in addition to the cleanliness of the sample.

Further, in an optional step (not shown in figure), the contamination/impurities particles released from the sample air may be trapped by a filter 302 by applying a vacuum through the filter holder 301 and filter 302. The trapped particles may be further analyzed to determine nature and chemical composition of the impurities particles.

According to an embodiment of the invention, the contamination/impurities particle may be present over surface of the sample 109. If number of contamination/impurities particles (i.e., the difference between the readings) released due to strike by the stream of clean air, or and the strike of ionized clean air generated by the ESD 203 is more than the predetermined threshold, the sample 109 may have too many contamination/impurities particle present over it, that it is not fit to be taken to a clean room or production facility. Hence, the sample 109 may be cleaned, and then the sample 109 may be again tested for cleanliness criteria. This process may be repeated till the cleanliness of the sample 109 is within cleanliness standard required in the production facility/clean room.

In an embodiment of the invention, the reading data may be automatically acquired by a computer (not shown in the drawing figures) attached to the apparatus and further processed to determine cleanliness of the sample 109. The computer may have appropriate software installed (in addition to display, memory, and processor), that may acquire the readings taken, process the readings, and automatically determine cleanliness of the sample 109.

In another embodiment of the invention, the functionality as well as the readings from the particle counter can be controlled by a Logic Programmable Controller (LPC) (not shown in the drawing figures) that includes a graphic display unit to interact with the operator. Moreover, the LPC can be connected to a computer with appropriate software to store, process and evaluate the results.

In another embodiment of the invention, the reading data may be manually read and processed by an operator (i.e., the difference between the readings may be manually carried by an operator) of the apparatus to determine cleanliness of the sample 109.

According to some embodiments of the invention methods and apparatus are provided for contamination detection for samples, products and tools used in/by high tech industries. Contamination detection has become increasingly significant, particularly with rapid evolution of high-tech industries. For example, semiconductor industry has developed technology for precisely producing microelectronic devices and integrated circuits. In order to reliably produce such products, highly stringent contamination standards must be maintained in production facilities of such products.

According to some embodiments of the invention methods and apparatus are provided for detecting contamination of products made or used in clean rooms. In an effort to control contamination during a production process, clean rooms are frequently used. A clean room is a room in which air filtration, air distribution, utilities, materials of construction, equipment, and other operating procedures are specified and regulated to control airborne particle concentrations to meet appropriate airborne particulate cleanliness classifications. Clean rooms are used extensively in semiconductor manufacturing, biotechnology, pharmaceutical, disk drive, aerospace and other fields that are very sensitive to environmental contamination.

According to some further embodiments of the invention methods and apparatus are provided for monitoring and maintaining the cleanliness/contamination levels in the clean rooms. Further, for maintaining the cleanliness/contamination levels in the clean room, it is important to test/inspect a sample for cleanliness standard, before sending the sample to the clean room. According to some further embodiments of the invention methods and apparatus are provided for testing cleanliness of a sample before sending the sample to the clean room.

In addition, in the mentioned industries it is customary to carry out preventive maintenance of manufacturing tools such as sputtering, CVD, etch, and other tools. As part of this procedure some of the parts require renovation and cleaning. Therefore, it is of high importance to be able to test cleanliness of the part before reinstalling it to a machine. According to some further embodiments of the invention methods and apparatus are provided for maintenance of cleanliness of manufacturing tools such as sputtering, CVD, etch, and other tools.

According to some further embodiments of the invention methods and apparatus are provided for detecting particles that are of a size of less than one micron, in contrast to conventional techniques, which fail to achieve the goal. Furthermore, these conventional techniques are very tedious and time consuming. The duration of the tests of the invention is usually between 2-5 minutes and up to 10 minutes, if required.

According to some further embodiments of the invention methods and apparatus are provided for determining the cleanliness of a sample, before shipping or taking the sample to clean room environment. According to some further embodiments of the invention methods and apparatus are provided for determining the cleanliness of the sample in a convenient and effective manner. One of the most important advantages is that the method is NDT (non-destructive testing) unlike LPC (liquid particle counter) or similar and the sample can be used immediately in a clean room, for example, with no additional processing or cleaning.

Figure 6A:
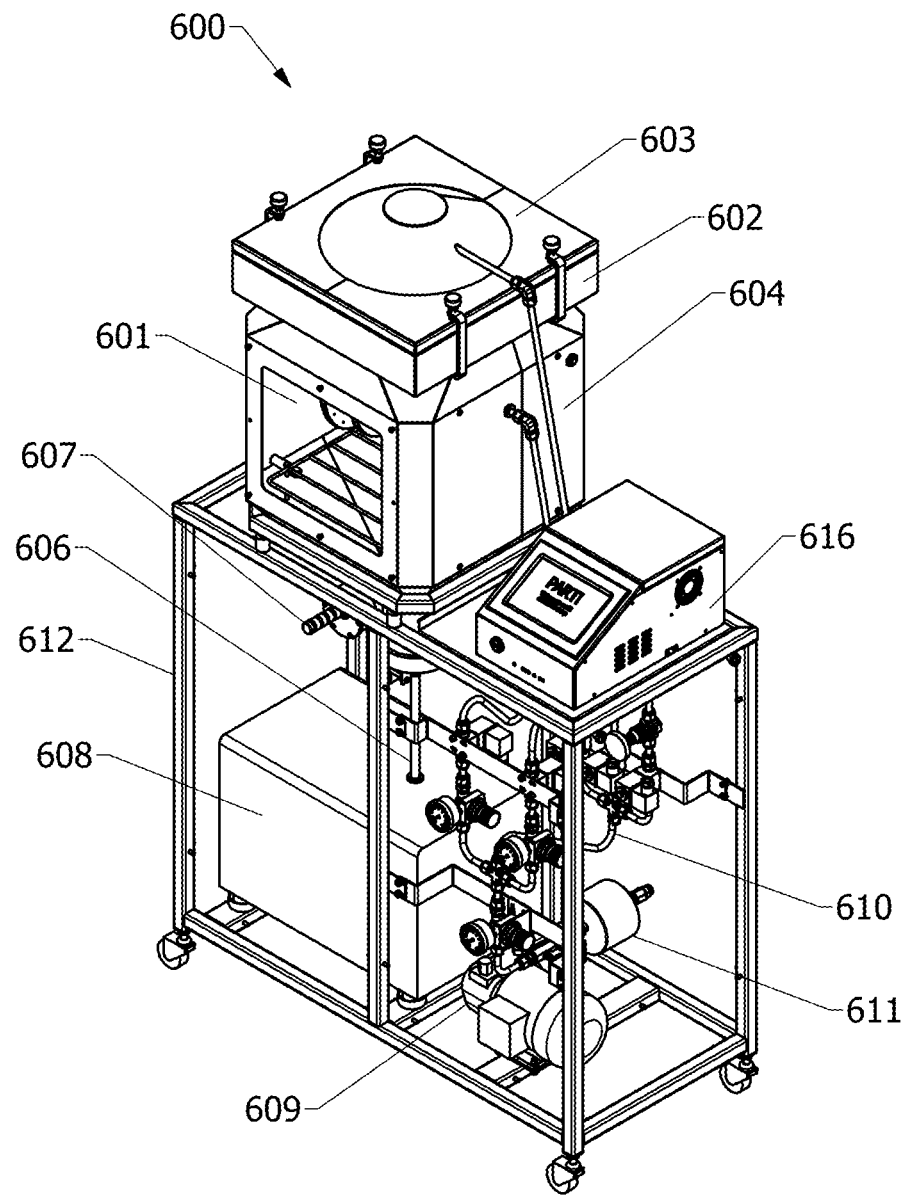
FIG. 6a is an another schematic diagram of an apparatus for determining cleanliness of a sample, according to an embodiment of the invention.

Reference is now made to FIG. 6a, which is another schematic diagram of an apparatus 600 for determining cleanliness of a sample, according to an embodiment of the invention. Apparatus 600 includes a HEPA filter 602 mounted with a dome 603 to supply clean dry air (CDA), which may be used to supply a constant flow of CDA through the HEPA filter 602 into a chamber 604.

Chamber 604 is further coupled to an isokinetic probe 606, which is connected to a laser type particle sensor 608. The particle sensor is controlled by the controller hardware 616 and software 618.

Figure 6B:
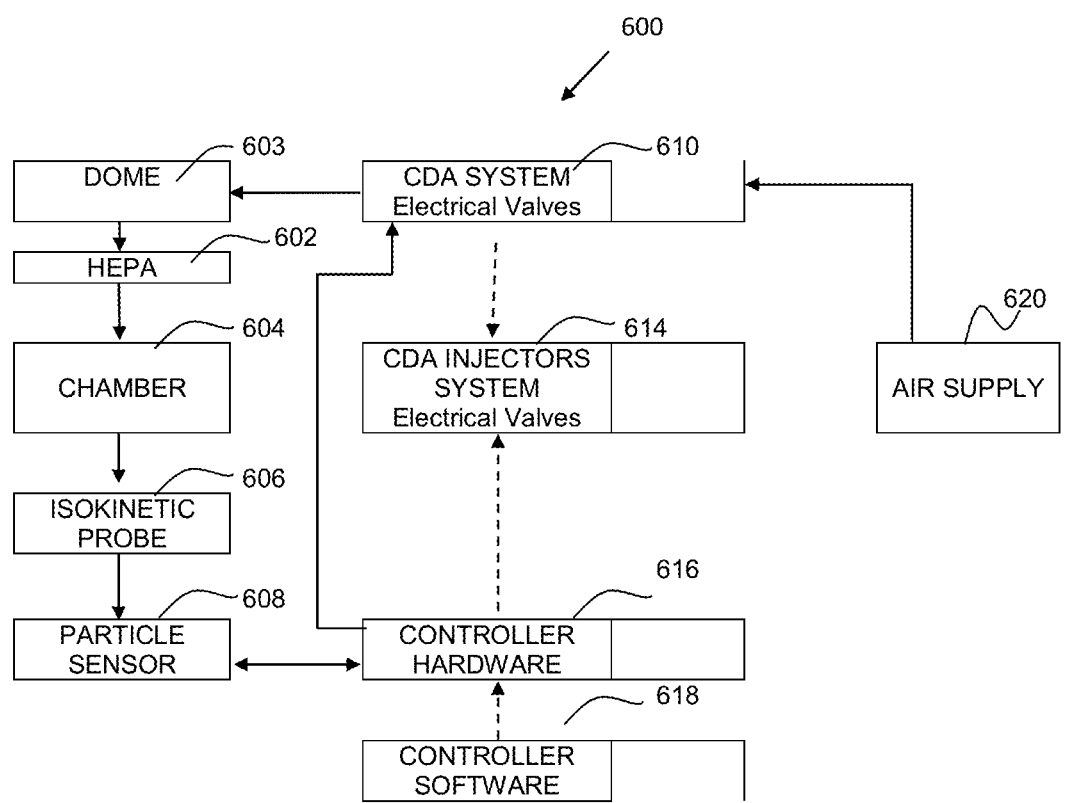
FIG. 6b is a simplified block diagram of an apparatus for determining cleanliness of a sample, according to an embodiment of the invention.

Reference is now made to FIG. 6B, which is another schematic diagram of an apparatus 600 (and subsystems 700 and 800) for determining cleanliness of a sample, according to an embodiment of the invention.

Apparatus 600 comprises a sampling chamber 604, similar or identical to chamber 101 (FIG. 1). The chamber is in fluid communication with a dome 603 and HEPA filter 602, typically mounted there-above. The HEPA filter receives air via an CDA system 610 having a set of electrical valves 803, 804, 805 from an air supply system 620 or compressor 850 (not shown). The electrical valves (803, 804, 805) are configured to provide CDA into the chamber at different flow rates controlled through needle valves 801, 802. The apparatus further comprises CDA injector system 614, configured to activate the CDA system for supplying a stream of clean air. The use of the different valves will be addressed below.

The apparatus further comprises a set of injectors (nozzles) 720, 725. The injectors are configured to supply a stream of air either through the top nozzle set 720, the bottom nozzle 725 or both.

The apparatus further comprises controller software 618 configured to run controller hardware 616. The controller hardware is also operative to activate/switch off the electrical valves of the air system and air injector system. The dome is configured to supply filtered air to the chamber.

Chamber 604 is further coupled to an isokinetic probe 606, which is connected to a laser type particle sensor 608. The particle sensor is controlled by the controller hardware 616 and software 618. Apparatus 600 further comprises a cart or trolley 612 for holding and easy maneuvering of the apparatus. The apparatus further comprises an in-line inlet HEPA filter 611.

In order for the laser type particle counter or sensor to operate it requires a vacuum device (pump or blower) to pull a vacuum though it. The particle counter or sensor can include its own vacuum device or can be such that needs an external vacuum device to provide the required vacuum. The vacuum device can be a conventional vacuum pump or a Venturi pump that is more adequate for a clean environment.

The apparatus of the invention is constructed and configured to perform non-destructive testing of cleanliness of a sample, such that after the testing methodology, the sample is ready for use. This is particularly important for clean room parts various clean room articles and clothing for clean room use and for manufacturing tool parts that can be tested and shipped without further additional processing.

Moreover, apparatus 600 of the invention is further constructed and configured to perform non-destructive removal of particles from a sample, such that after the particle removal methodology, the sample is ready for use. This is particularly important for clean room parts and articles or clothing for clean room use.

The invention further provides apparatus 600 for determining cleanliness of a sample. The apparatus includes HEPA filter unit 602 with a dome connected to a CDA supply 603, chamber 604, a nozzle set (900), similar or identical to the nozzle set shown in the drawings and a particle counter 104 and/or particle sensor 608. The chamber includes a sample holder (jig) or an integrated sample holder and nozzle for holding a sample. In one embodiment a customized sample holder (710) to test specialized cassettes used among others to hold silicon wafers or magnetic disks. This device is connected to the bottom nozzle 725, and serves a dual purpose to supply air through orifices and to hold the sample, (cassette) a detailed description will be given later (FIG. 9B).

Figure 9A:
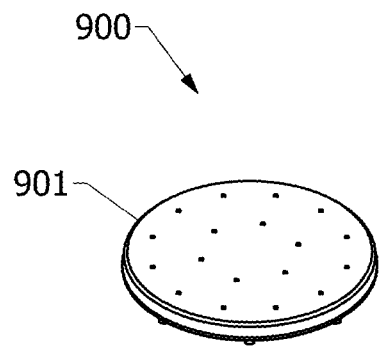
FIG. 9A is a simplified diagram of a nozzle head, according to an embodiment of the invention.
Figure 9B:
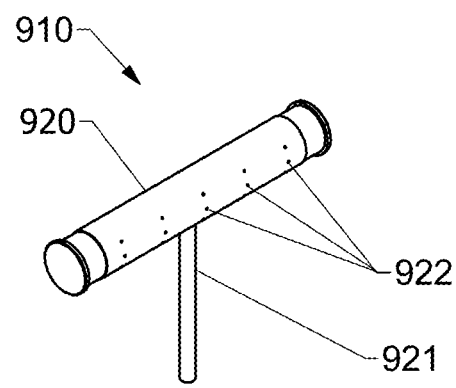
FIGS. 9B and 9C are simplified diagrams of integrated sample holders and air supply devices, according to some embodiments of the invention.

FIG. 9A shows is a simplified diagram of a nozzle head 900 having a shower face 901, according to an embodiment of the invention.

The nozzle set is located in the chamber, and is configured to direct a stream of clean air into the sample. The stream of clean air is operated through an in-line HEPA filter to avoid generation of particles. The particle counter is coupled with the chamber, and configured to count particles released from the sample. The operation of the full system is managed by a electronic controller.

Figure 7:
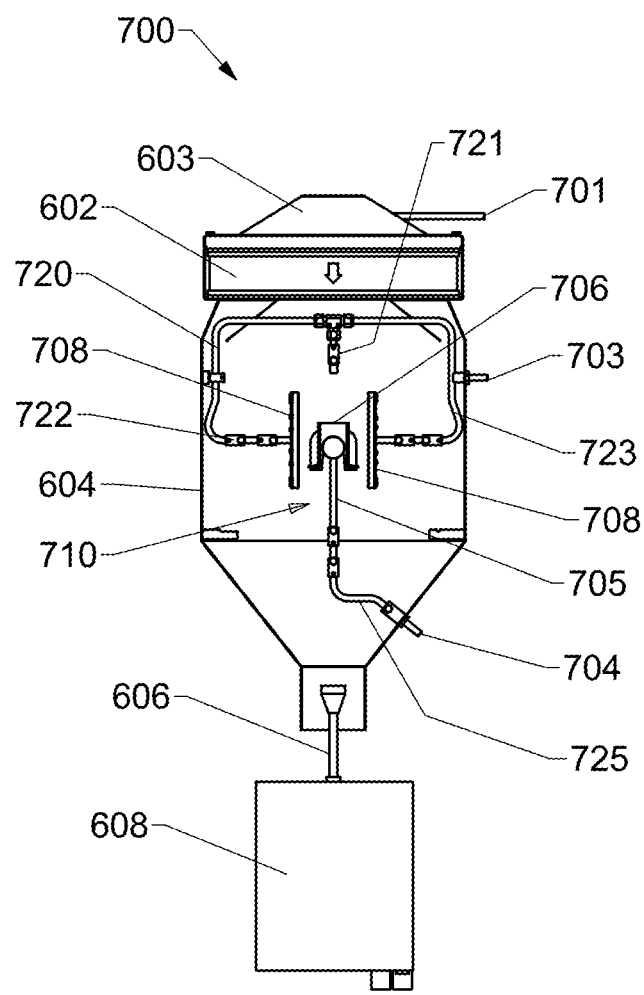
FIG. 7 is a simplified diagram of a front view of an apparatus for determining cleanliness of a sample, according to an embodiment of the invention.

Reference is now made to FIG. 7, which is a simplified diagram of a front view of an apparatus 700 for determining cleanliness of a sample, according to an embodiment of the invention.

A dome 603 is configured to supply CDA through an HEPA filter 602 to a chamber 604. The air is supplied through inlet 701. The chamber 604 is in tandem with an isokinetic probe 606 and a particle sensor 608.

The figure shows a upper set of nozzles 720 which is connected to the chamber 604 and CDA is supplied though inlet 703. The set on nozzles 720 from air supply inlet 704 to a sample holder 705, which is configured to supply a stream of high velocity CDA over the sample 706, through nozzles 721, 722, 723 all together or a combination of these, if one or more of these nozzles can be caped if not used for a particular test. The figure also shows air showers connected to nozzles 722, 723.

Furthermore, the figure shows a bottom nozzle 725 configured to supply a stream of high velocity CDA over the sample. This nozzle can be used separately or together with nozzle set 720.

In an embodiment of the invention, the bottom nozzle 725 is connected to a customized sample holder (710) to test specialized cassettes used to hold silicon wafers or magnetic disks. This device serves a dual purpose to supply air through orifices and to hold the sample, (cassette) a detailed description will be given later (FIG. 9B).

Figure 8:
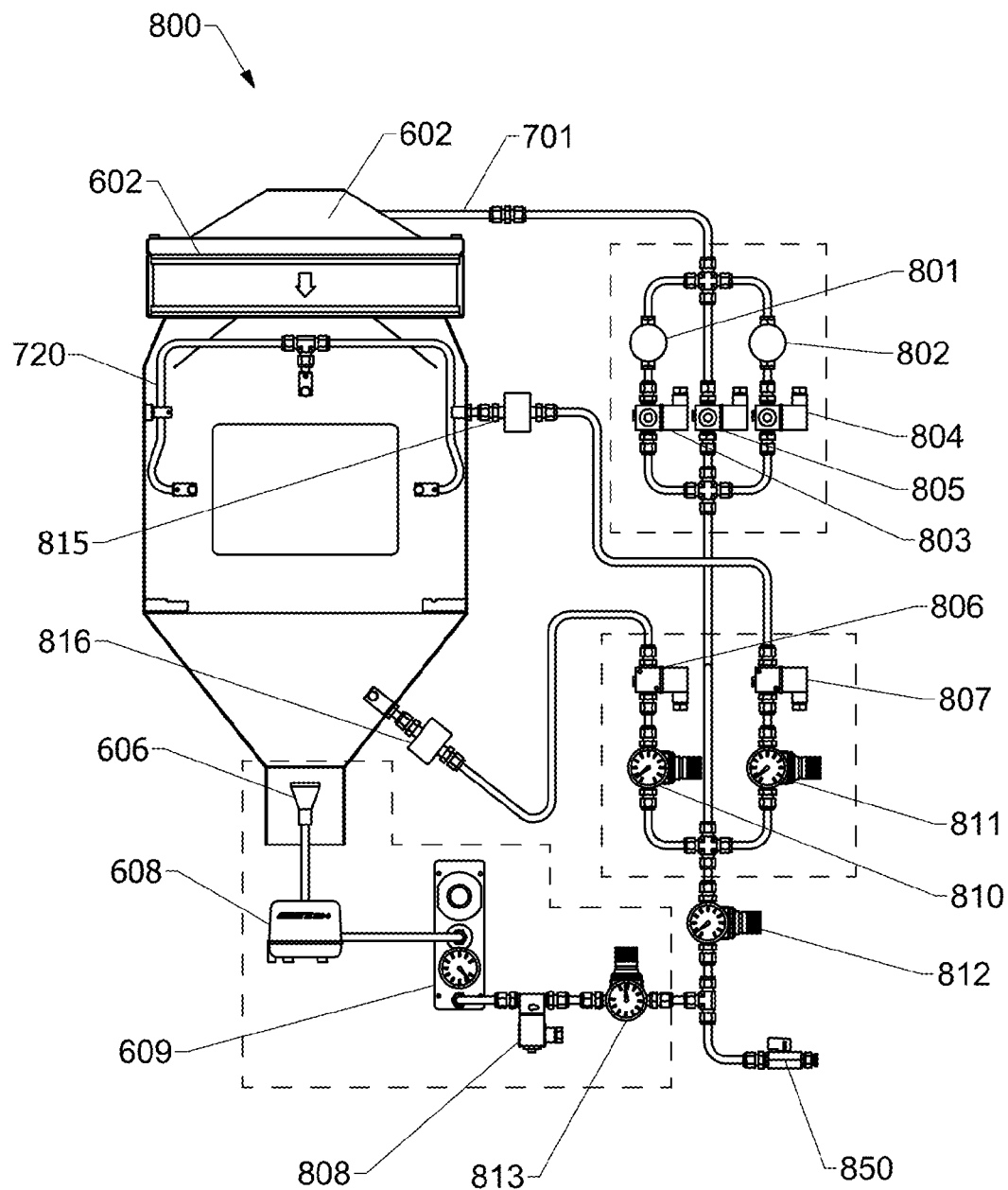
FIG. 8 is a simplified diagram an apparatus for determining cleanliness of a sample including a detailed front view of an air supply system, according to an embodiment of the invention.

Turning to FIG. 8, there is seen a simplified diagram an apparatus 800 for determining cleanliness of a sample including a detailed front view of an air supply system 610, according to an embodiment of the invention;

The system comprises of a dome 603 to supply CDA through an HEPA filter 602 to a chamber 604. The air is supplied through inlet 701. The HEPA filter receives air via a CDA system 610 having a set of electrical valves 803, 804, 805 through inlet 850 from an air supply (not shown). The electrical valves (803, 804, 805). Are configured to provide CDA into the chamber at different flow rates controlled through needle valves 801, 802.

The chamber 604 is in tandem with an isokinetic probe 606 and a particle sensor 608, connected to a vacuum pump. In the figure, a Venturi pump 609 is show that is activated by a valve 808 and the supply air pressure, is controlled by regulator 813. Apparatus 600/700/800 is configured to enable determination of cleanliness of a sample. The set of needle valves 802, 801 providing the flow to the HEPA filter are configured to deliver flow according to the following:

Setting1: Needle valve 801 and electrical valve 803 are used to supply a constant flow of CDA (usually 2-3 cfm) though the HEPA filter while measuring particles released from the sample.

Setting 2: Needle valve 802 and electrical valve 804 deliver an increased flow (3-4 CFM) to provide positive pressure to the chamber 604 used during inserting and removing the sample.

Setting 3: Electrical valve 805 is used to flush the chamber 604 at an increased flow rate of 6-12 CFM as set by the pressure regulator 812.

The apparatus further comprises a set of injectors (nozzles) 721, 722, 723, 725 connected to in-line HEPA filter units 815, 816 activated by electrical valves 806, 807 the pressure to the injectors is regulated by pressure regulators 810 and 811, while regulator 812 controls the total inlet pressure of the system.

The method includes:

1) taking a reference reading of the empty chamber, while clean air is flowing through a HEPA filter into the chamber (setting 1);

2) placing a sample into a chamber (setting 2);

3) taking a reading of particles count released from the sample, while clean air is flowing thru an HEPA filter into the chamber (setting 2); and 4) directing a stream of high velocity clean air through the set of nozzles 725 and or 720 over the sample, and taking a reading of particles count of the sample.

5) The method may further include directing a stream of ionized air over the sample, and taking a reading of particles count released from the sample, while an electrostatic discharge device (ESD) is activated.

The cleanliness of the sample based upon calculating the difference of the readings, taking into account the blank reading and the particles count at each steep as well as the total.

Steps 3 and 4 described above may be repeated multiple times.

The various recipes (testing procedures) of the controller software are randomly named after capital cities, a method used by the developers for operational convenience.

The method and apparatus described above is managed by electronic controller hardware 616 system, that is used to operate apparatus 600 or 100. A microcomputer board, a programmable controller, a laptop computer or an equivalent device (collectively termed controller hardware 616) is equipped with appropriate software 618 is used to control the operation of the apparatus, to acquire the readings of the particle counter and/or particle sensor 608, and further processes the data to determine cleanliness of the sample.

The readings of the particle counter (data) are automatically acquired by the electronic control system. The user has the capability to create various testing procedures, (recipes) using the control system, so it suits different types of samples.

One embodiment of the present provides a method for removing particles from a sample by short pulses (1-3 seconds step 2) of high velocity air streams, through the nozzles set 720 and or 725 and subsequent waiting periods of (30-60 seconds—step 3), to measure the released particles while clean air is always flowing through the HEPA filter (setting 1) from top to bottom of the chamber 604. In many cases this method was found to exhibit higher sensitivity (five to ten times) compared to longer durations of step 2. Ionized air flowing either though the nozzles or though the HEPA filter can be used, if necessary.

According to one embodiment of the present, the controller hardware 618 comprises a UDOO, a RASPBERRY-PI, a PANDABOARD microcomputer board or similar connected to a touch screen running on LINUX operation system and loaded with software 618.

Further, in an embodiment of the invention, the apparatus 600 may include an Electrostatic Precipitator device (ESP) 607 with a removable electron microscope holder coated with a detachable carbon sticker (not shown), to which high voltage (5 KV) is applied in order to catch particles released from the sample for analyzing the chemical composition of trapped particles the carbon sticker (not shown) can be further removed from the device 607. Thus, the nature and chemical composition of the particles can be further determined by conventional analytical methods.

According to some embodiments, the carbon sticker has self-adhesive on both sides, one side is sticks to the electron microscope holder and the other side faces the chamber, so particles get stick to it.

Figure 9C:
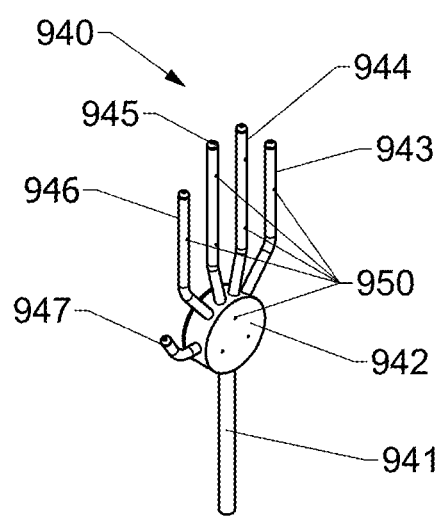

FIG. 9A is a simplified diagram of a nozzle head (air shower), according to an embodiment of the invention; and FIGS. 9B and 9C are simplified diagrams of integrated sample holders and air supply devices, according to some embodiments of the invention.

FIG. 9B is a simplified diagram of a customized sample holder 910 to test specialized cassettes used to hold silicon wafers or magnetic disks. This device consists of a cylinder 920 that serves a dual purpose: 1) to hold the sample, (cassette 706) and to supply air through a number (15-30) of small orifices (1-2 mm) 922 configured so it delivers high velocity air over the sample from an air inlet conduit 921. Furthermore, this device is used in conjunction with nozzle set 720 and air showers 708 (also shown in FIG. 9A). This setup enables testing the sample internally as well as externally at the same time or each separately by activating the proper valves (806, 807) by the controller 616.

FIG. 9C is a simplified diagram of a customized sample holder 710 to test clean room gloves. This device 940 consists of an air inlet conduit 941, an air distributor 942 and a set of arms (943, 944, 945, 946 and 947). The arms are configured to fit standard sized clean room gloves. The arms are further configured to deliver high velocity air through a number (3-10) of small orifices 950 (1-2 mm) on each arm. The device serves a dual purpose to hold the sample (glove) and to deliver air as explained above. Furthermore, this device is used in conjunction with nozzle set 720 and air showers 708 (also shown in FIG. 9A). This setup enables testing the sample internally as well as externally at the same time or each separately by activating the proper valves (806, 807) by the controller 616.

Sample holder 710 thus provides a dual purpose of holding the sample and supplying an airstream within and/or to the sample.

Figure 9D:
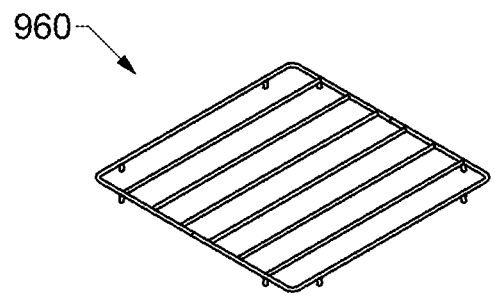
FIG. 9D is a simplified diagram of a general purpose grid sample holder, according to an embodiment of the invention.
Figure 9E:
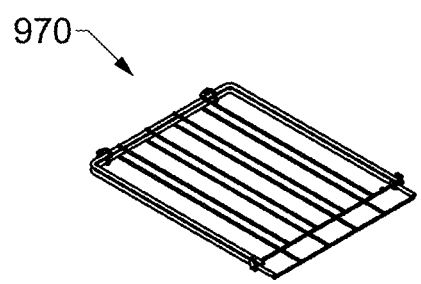
FIG. 9E is a simplified diagram of a clean room paper grid sample holder, according to an embodiment of the invention.
Figure 9F:
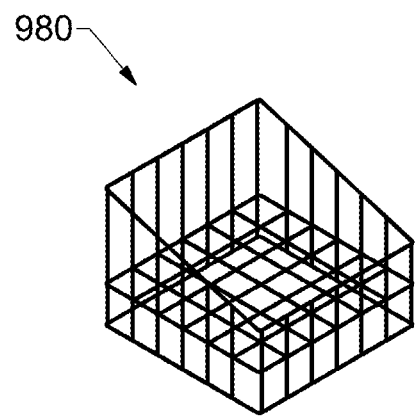
FIG. 9F is a simplified diagram of a basket sample holder, according to an embodiment of the invention.

Additional sample holders designed to serve special purposes such as testing clean room papers, towels etc. are also shown in FIGS. 9D, 9E and 9F.

FIG. 9D is a simplified diagram of a general purpose grid sample holder 960, according to an embodiment of the invention.

FIG. 9E is a simplified diagram of a clean room paper grid sample holder 970, according to an embodiment of the invention.

FIG. 9F is a simplified diagram of a basket sample holder 980, according to an embodiment of the invention.

Devices, holders and jigs depicted in FIGS. 9A-9F are manufactured from metals such as stainless steel, aluminum, titanium, copper and plastics materials or a combination.

Also, while the flowcharts have been discussed and illustrated in relation to a particular sequence of events, it should be appreciated that changes, additions, and omissions to this sequence can occur without materially affecting the operation of the invention.

A number of variations and modifications of the invention can be used. It would be possible to provide for some features of the invention without providing others.

The invention, in various embodiments, configurations, and aspects, includes components, methods, processes, systems and/or apparatus substantially as depicted and described herein, including various embodiments, sub-combinations, and subsets thereof. Those of skill in the art will understand how to make and use the invention after understanding the present disclosure. The invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A non-destructive method for determining cleanliness of a sample, the method comprising:
   an operating apparatus,
   wherein the operating apparatus comprises:
   a chamber having a door and a sample holder or an integrated sample jig for holding both the sample in said chamber and providing a high velocity air stream over the sample; in said chamber,
   a HEPA filter unit with a blower or a dome to provide clean dry air (CDA) disposed above said chamber and in fluid connection with said chamber; said blower or dome adapted to provide a constant flow to said chamber,
   a nozzle set activated by a set of valves to provide a stream of high velocity clean air or short pulses of high velocity clean air over the sample, wherein the air to the nozzles set is provided through in-line HEPA filter units,
   a valve coupled to an electrostatic discharge device (ESD) for generating ionized air, in fluid connection with said nozzle set, located in said chamber, said nozzle set configured to direct a stream of air via said in-line HEPA filter unit onto the sample,
   a particle counter, coupled with the chamber, configured to count particles passed in a stream of air from said sample to said particle counter, and
   a programmable controller for operating said apparatus, and
   an electrostatic precipitator device (ESP) with a removable electron microscope holder coated with a detachable carbon sticker to which high voltage (5 KV) is applied in order to catch particles released from the sample for analyzing the chemical composition of trapped particles:
   wherein the operating apparatus determines the cleanliness of the sample by the following steps:
   a) providing a continuous flow of clean air into the chamber; through the HEPA filter,
   b) taking a reference reading of particle counts while said chamber is empty,
   c) introducing said sample into the chamber, and
   d) taking a first reading of a particle count received from all sides of said sample in said chamber to determine loose particles in a particle size range of 0.1 microns up to 5 microns associated with said sample.

2. The method of claim 1, wherein said sample is a generally three-dimensional sample.

3. The method of claim 1, further comprising:
   e) directing a stream of ionized air over said sample from a valve coupled to an electrostatic discharge device (ESD) for generating said ionized air, in fluid connection with said set of nozzles;
   f) taking a second reading of particles count of said sample; and
   g) calculating a difference between the first reading and the second reading thereby determining said cleanliness of said sample based upon said difference.

4. The method of claim 3, wherein a third reading is taken during said directing step and wherein said cleanliness of said sample is calculated based upon a difference between the third reading and the second reading, or between the three readings, while taking into account said reference reading.

5. The method of claim 4, wherein the determining comprises comparing the difference with a predetermined threshold.

6. The method of claim 4, wherein the difference represents an impurities particles count.

7. The method of claim 1, further comprising:
activating the electrostatic precipitator device (ESP) with a removable electron microscope holder coated with a detachable carbon sticker to which high voltage (5 KV) is applied in order to catch particles released from the sample for analyzing the chemical composition of trapped particles; and
trapping the impurities particles released from the sample due to said stream of ionized air.

8. The method of claim 7, further comprising analyzing the trapped particles to determine nature and chemical composition of the impurities particles.

9. The method of claim 1, wherein the sample is selected from at least one of a metal part, quartz part, ceramic part, and plastic part, a machine part, a tool, a clean room gown, a clean room glove a clean room towel, a silicon wafer, and a magnetic disk.

10. The method of claim 9, wherein said sample, once tested, is ready for use in a clean room following said method.

11. An apparatus for determining cleanliness of a sample, the apparatus comprising:
a chamber having a door and a sample holder or an integrated sample jig for holding both the sample in said chamber and providing a high velocity air stream over the sample; in said chamber;
a HEPA filter unit with a blower or a dome to provide clean dry air (CDA) disposed above said chamber and in fluid connection with said chamber; said blower or dome adapted to provide a constant flow to said chamber;
a nozzle set activated by a set of valves to provide a stream of high velocity clean air or short pulses of high velocity clean air over the sample, wherein the air to the nozzle set is provided through in-line HEPA filter units;
a valve coupled to an electrostatic discharge device (ESD) for generating ionized air, in fluid connection with said nozzle set, located in said chamber, said nozzle set configured to direct a stream of air via said in-line HEPA filter unit onto the sample;
a particle counter, coupled with the chamber, configured to count particles passed in a stream of air from said sample to said particle counter; and
a programmable controller for operating said apparatus, and
an electrostatic precipitator device (ESP) with a removable electron microscope holder coated with a detachable carbon sticker to which high voltage (5 KV) is applied in order to catch particles released from the sample for analyzing the chemical composition of trapped particles.

12. The apparatus of claim 11, wherein the sample is selected from at least one of a metal part, quartz part, ceramic part, a plastic part, a machine part, a tool, a clean room gown, a clean room glove a clean room towel, a silicon wafer and a magnetic disk.

13. The apparatus of claim 11, wherein the nozzle set comprises a shower head connected to an in-line HEPA filter unit.

14. The apparatus of claim 11, wherein the nozzle set comprises a nozzle and a shower head connected to an in-line HEPA filter unit.

15. The apparatus of claim 11, wherein the chamber further comprises a filter detachably located in a filter holder for trapping particles released from the sample due to the stream of air by applying a vacuum through the filter.

16. The apparatus of claim 15, wherein the filter is removable for analyzing the chemical composition of trapped particles.

17. The apparatus of claim 11, wherein said valve is a Venturi valve for supplying a stream of clean air or ionized air.

18. The apparatus of claim 11, wherein said particle counter is a laser type particle counter.

19. The apparatus of claim 18, wherein said laser type particle counter particle counter requires an external vacuum pump.

20. The apparatus of claim 19, wherein said external vacuum pump is a Venturi type pump.

21. The apparatus of claim 11, wherein said ESD device is adapted for activation by supplying a voltage thereto to provide a constant flow of ionized air to said chamber.

22. The apparatus of claim 11, wherein said chamber and said particle counter are connected via a counter isokinetic probe.

23. The apparatus of claim 11, wherein said ESD device is located inside the chamber and adapted for activation by supplying a voltage thereto to provide a constant flow of ionized air to said chamber.

* * * * *